United States Patent

Morales

[11] Patent Number: 6,051,002
[45] Date of Patent: Apr. 18, 2000

[54] STENT CRIMPING DEVICE AND METHOD OF USE

[75] Inventor: Stephen A. Morales, Mountain View, Calif.

[73] Assignee: Advanced Cardiovascular Systems, Inc., Santa Clara, Calif.

[21] Appl. No.: 09/169,270

[22] Filed: Oct. 9, 1998

[51] Int. Cl.[7] .................................................. A61F 11/00
[52] U.S. Cl. ............................................................ 606/108
[58] Field of Search ................................... 606/108, 194, 606/198; 623/1, 11, 12

[56] References Cited

U.S. PATENT DOCUMENTS

| | | |
|---|---|---|
| 696,289 | 3/1902 | Williams . |
| 4,468,224 | 8/1984 | Enzmann et al. . |
| 4,576,142 | 3/1986 | Schiff . |
| 4,644,936 | 2/1987 | Schiff . |
| 4,681,092 | 7/1987 | Cho et al. . |
| 4,697,573 | 10/1987 | Schiff . |
| 4,901,707 | 2/1990 | Schiff . |
| 4,907,336 | 3/1990 | Gianturco . |
| 5,189,786 | 3/1993 | Ishikawa et al. . |
| 5,437,083 | 8/1995 | Williams et al. . |
| 5,546,646 | 8/1996 | Williams et al. . |
| 5,626,604 | 5/1997 | Cottone, Jr. . |
| 5,653,691 | 8/1997 | Rupp et al. . |
| 5,672,169 | 9/1997 | Verbeek . |
| 5,738,674 | 4/1998 | Williams et al. . |
| 5,746,764 | 5/1998 | Green et al. . |
| 5,783,227 | 7/1998 | Dunham . |
| 5,785,715 | 7/1998 | Schatz . |
| 5,836,952 | 11/1998 | Davis et al. . |

FOREIGN PATENT DOCUMENTS

| | | |
|---|---|---|
| 159065 | 2/1921 | United Kingdom . |
| WO 98/14120 | 4/1998 | WIPO . |
| WO 98/19633 | 5/1998 | WIPO . |

OTHER PUBLICATIONS

U.S. Patent Application Serial No. 08/795,335 filed Feb. 4, 1997 No Drawings are enclosed.
U.S. Patent Application Serial No. 08/837,771 filed Apr. 22, 1997.
U.S. Patent Application Serial No. 08/893,936 filed Jul. 15, 1997.
U.S. Patent Application Serial No. 08/962,632 filed Nov. 3, 1997.
U.S. Patent Application Serial No. 09/024,910 filed Feb. 17, 1998.
U.S. Patent Application Serial No. 09/030,261 filed Feb. 25, 1998.
U.S. Patent Application Serial No. 09/063,905 filed Apr. 21, 1998.
U.S. Patent Application Serial No. 09/063,587 filed Apr. 21, 1998.
U.S. Patent Application Serial No. 09/069,010 filed Apr. 28, 1998.
U.S. Patent Application Serial No. 09/069,011 filed Apr. 28, 1998.
U.S. Patent Application Serial No. 09/072,925 filed May 5, 1998.
U.S. Patent Application Serial No. 09/123,844 filed Jul. 28, 1998 Lost? Not available.
The eXTraordinary Stent, C.R. Bard Brochure (Undated).

*Primary Examiner*—Michael Buiz
*Assistant Examiner*—Vy Q. Bui
*Attorney, Agent, or Firm*—Fulwider Patton Lee & Utecht

[57] ABSTRACT

A pivotally-engageable device for enabling uniform and tight crimping of an intravascular stent onto a balloon catheter assembly. The stent crimping device includes at least one releasable loop portion that enables the stent and catheter assembly to be supported therein. The ends of the loop portion are moved in opposite directions thereby reducing the size of loop radially inwardly to uniformly and tightly crimp the stent onto the balloon catheter assembly.

12 Claims, 7 Drawing Sheets

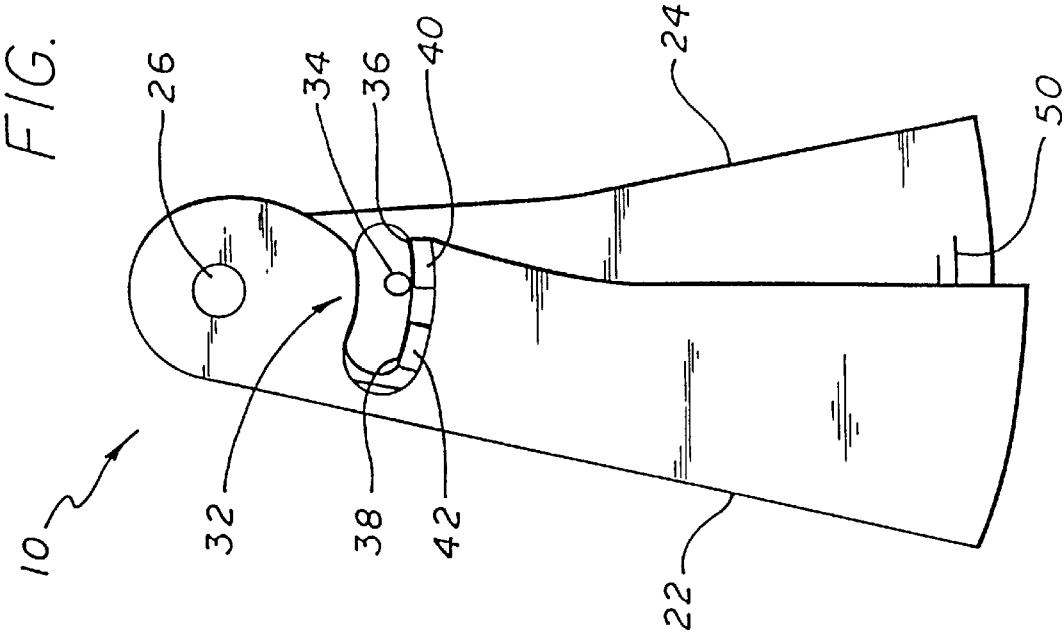
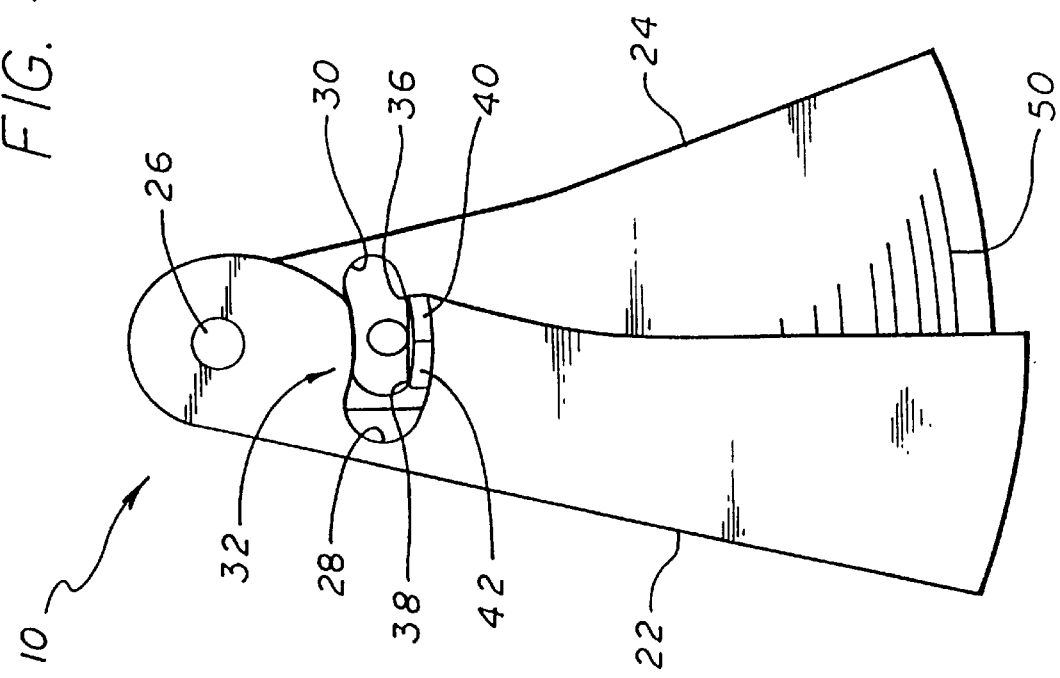

FIG. 11
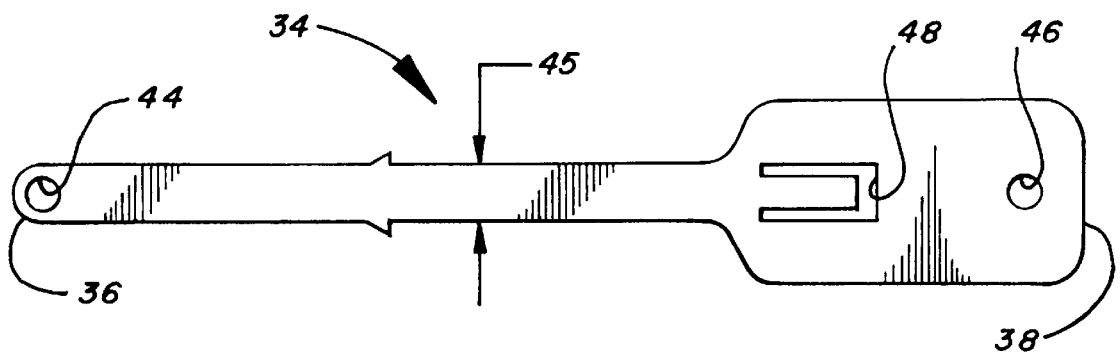
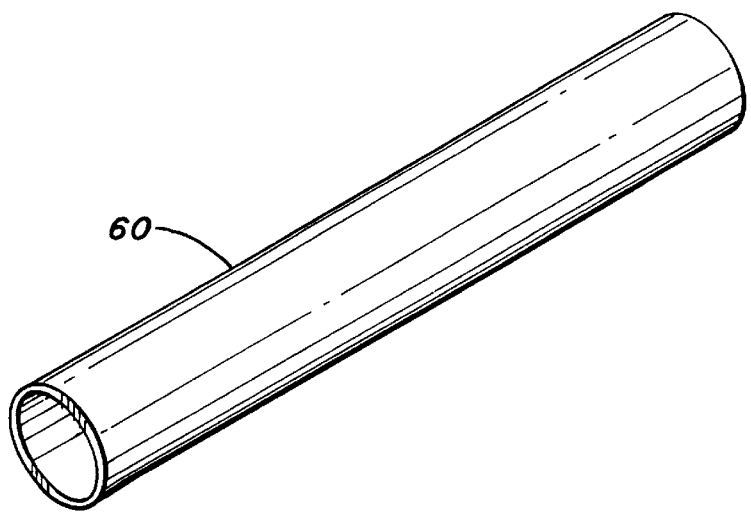
FIG. 12A

STENT CRIMPING DEVICE AND METHOD OF USE

BACKGROUND OF THE INVENTION

This invention relates to a stent crimping device of the type that will enable the user to uniformly and tightly crimp a stent onto the distal end of a catheter assembly, for example of the kind used in a typical percutaneous transluminal coronary angioplasty (PTCA) procedure or percutaneous transluminal angioplasty (PTA) procedure.

In a typical PTCA procedure, for compressing lesion plaque against the artery wall to dilate the artery lumen, a guiding catheter is percutaneously introduced into the cardiovascular system of a patient through the brachial or femoral arteries and advanced through the vasculature until the distal end is in the ostium. A guide wire and a dilatation catheter having a balloon on the distal end are introduced through the guiding catheter with the guide wire sliding within the dilatation catheter. The guide wire is first advanced out of the guiding catheter into the patient's coronary vasculature, and the dilatation catheter is advanced over the previously advanced guide wire until the dilatation balloon is properly positioned across the lesion. Once in position across the lesion, a flexible, expandable, preformed balloon is inflated to a predetermined size at relatively high pressures to radially compress the atherosclerotic plaque of the lesion against the inside of the artery wall and thereby dilate the lumen of the artery. The balloon is then deflated to a small profile, so that the dilatation catheter can be withdrawn from the patient's vasculature and blood flow resumed through the dilated artery. While this procedure is typical, it is not the only method used in angioplasty. Other methods for compressing plaque or removing it are known, such as atherectomies or use of plaque dissolving drugs.

In angioplasty procedures of the kind referenced above, a restenosis of the artery may develop over several months, which may require another angioplasty procedure, a surgical bypass operation, or some method of repairing or strengthening the area. To reduce the likelihood of the development of restenosis and strengthen the area, a physician can implant an intravascular prosthesis for maintaining vascular patency, typically called a stent. A stent is a device used to hold tissue in place in a vessel or to provide a support for a vessel to hold it open so that blood flows freely. A variety of devices are known in the art for use as stents, including expandable tubular members, in a variety of configurations, that are able to be crimped onto a balloon catheter, and expanded after being positioned intraluminally on the balloon catheter, and that retain their expanded form. Typically, the stent is loaded and crimped onto the balloon portion of the catheter, and advanced to a location inside the artery at the lesion. The stent is then expanded to a larger diameter, by the balloon portion of the catheter, to implant the stent in the artery at the lesion. Examples of stents and delivery catheters of the type described herein are disclosed in more detail in U.S. Pat. No. 5,102,417 (Palmaz); U.S. Pat. No. 5,569,295 (Lam); and U.S. Pat. No. 5,514,154 (Lau et al.).

If the stent is not effectively crimped onto the catheter balloon portion when the catheter is advanced in the patient's vasculature, the stent may move or possibly slide off the catheter balloon portion in the coronary artery prior to expansion, and may block the flow of blood, requiring procedures to remove the stent.

In procedures where the stent is placed over the balloon portion of the catheter, the stent must be compressed or crimped onto the balloon portion to prevent the stent from sliding off the catheter when the catheter is advanced in the patient's vasculature. In the past this crimping was often done by hand, which does not provide optimum results due to the uneven force being applied, resulting in non-uniform crimps. In addition, it was difficult to judge when a uniform and reliable crimp had been applied. Though some tools, such as ordinary pliers, have been used to crimp the stent, these tools have not been entirely adequate in achieving an effective crimp. Moreover, an ineffectively crimped stent may result in an ineffectively expanded stent in the vessel or artery, which is undesirable.

SUMMARY OF THE INVENTION

The invention is directed to a crimping tool and method of use for enabling effective crimping of a stent onto the balloon portion of a catheter in order to better secure a stent onto the catheter for low-profile delivery of the stent through the patient's vascular system. The present invention attempts to solve several problems associated with crimping stents onto balloon catheters.

In an exemplary embodiment of the present invention, the stent crimping tool includes a pair of handles pivotally engaged such that a first handle member receives within it a second handle member. The invention further includes a cylindrical loop crimping member comprising a flexible sheet or film of material, such as a thin piece of Mylar material, in the form of a loop. The ends of the loop are attached respectively to the first handle and the second handle. An application of force on the handles causes the prospective ends of the cylindrical loop to move in opposite directions thereby providing a tension force which results in reducing the opening of the cylindrical loop.

The invention further provides for mounting a stent on the balloon portion of a catheter, and positioning the stent and balloon portion of the catheter within the cylindrical loop. As the handles of the stent crimping tool are compressed, the ends of the cylindrical loop are pulled in opposite directions thereby reducing the size of the loop and tightly compressing the stent in a uniform manner on the balloon portion of the catheter.

By releasing the handles, which are biased open, the cylindrical loop returns to its original size, thereby permitting the stent and balloon portion of the catheter to be removed from the cylindrical loop.

In one embodiment of the invention, the cylindrical loop is formed from a substantially non-stretchable plastic material having a high tensile strength and a low modulus.

One of the handles of the stent crimping tool includes reference indicia relative to the other handle member so that the reference indicia correspond to the crimping diameter of the cylindrical loop. As the two handles are compressed one into the other, the reference indicia will indicate the size or diameter of the cylindrical loop, and thereby determine the ultimate travel and thus, the resultant crimped diameter of the stent onto the balloon portion of the catheter.

These and other advantages of the invention will become more apparent from the following detailed description thereof when taken in conjunction with the accompanying drawings.

BRIEF DESCRIPTION OF THE DRAWINGS

FIG. 4 is a plan view depicting the first and second handle members pivotally engaged so that the cylindrical loop is positioned for receiving a stent for crimping onto the balloon portion of a catheter.

FIG. 5 is a plan view depicting the second handle member squeezed into the first handle member thereby restricting the diameter of the cylindrical loop which provides the crimping force on the stent.

FIG. 11 is a plan view depicting one preferred embodiment of the cylindrical loop in an uncoiled and flattened configuration.

FIGS. 12A–12C are perspective views depicting various embodiments of protective sheaths.

DETAILED DESCRIPTION OF THE PREFERRED EMBODIMENTS

Figure 1:
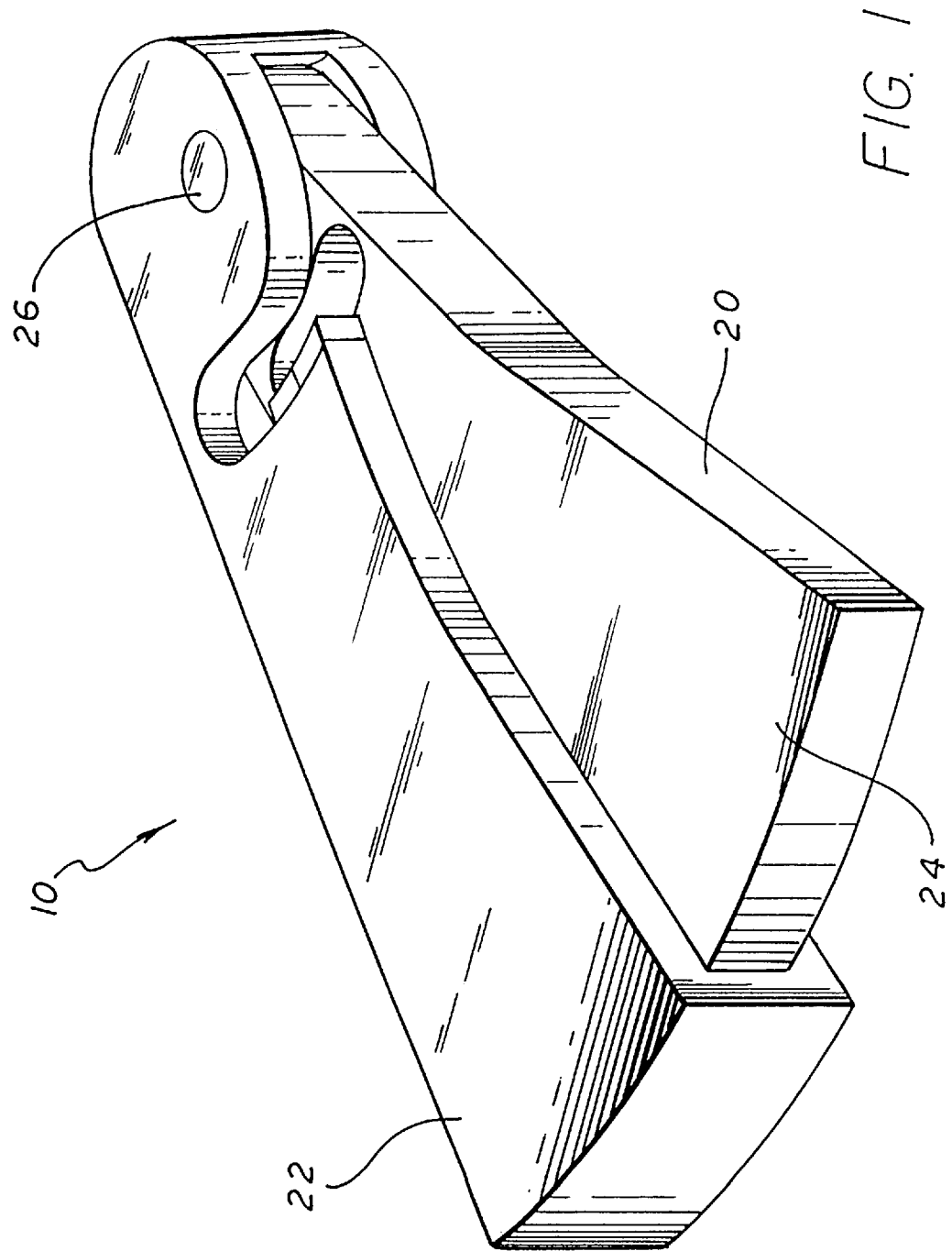
FIG. 1 is a perspective view of an exemplary embodiment of the present invention, in which the pivotally-engaging member is pivoted into engagement with the receiving member.
Figure 2:
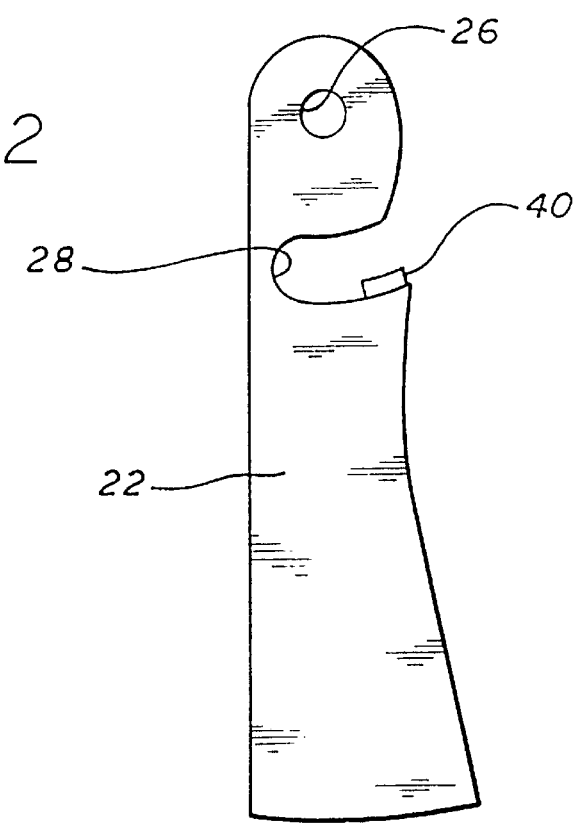
FIG. 2 is a plan view of the first handle member of the crimping tool.
Figure 3:
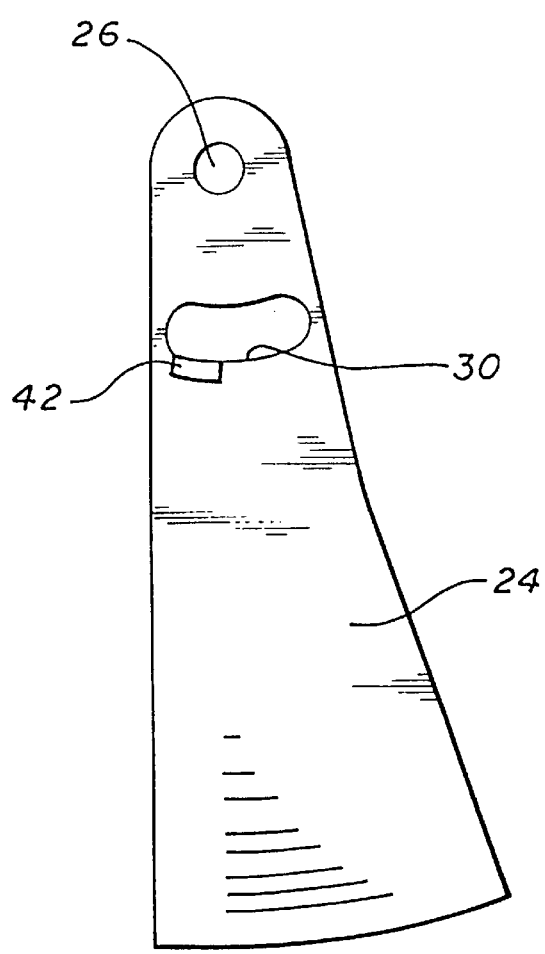
FIG. 3 is a plan view depicting the second handle member of the crimping tool, which is configured for slidably engaging the first handle member of FIG. 2.
Figure 6:
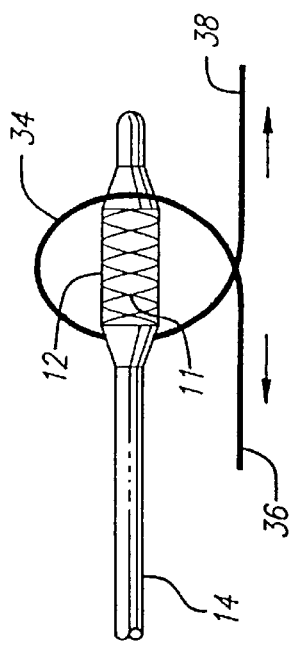
FIGS. 6–9 are side elevational views depicting a series of crimping steps wherein the cylindrical loop gradually tightens onto the stent thereby crimping it onto the balloon portion of the catheter as the loop ends are moved in opposite directions.
Figure 7:
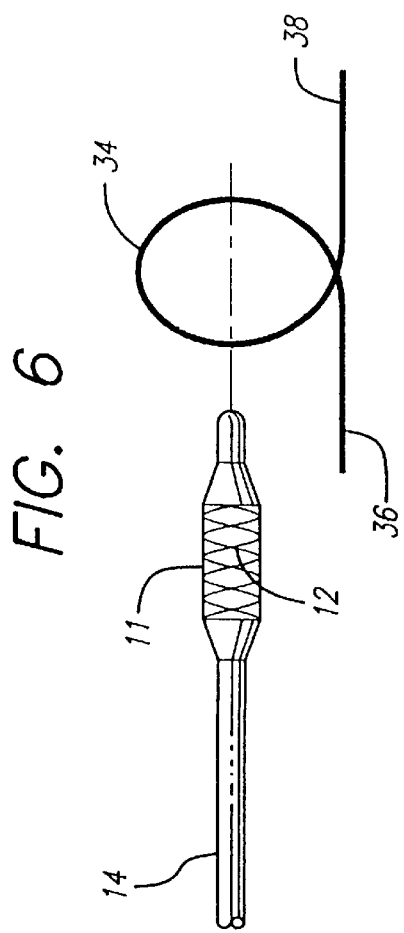
Figure 9:
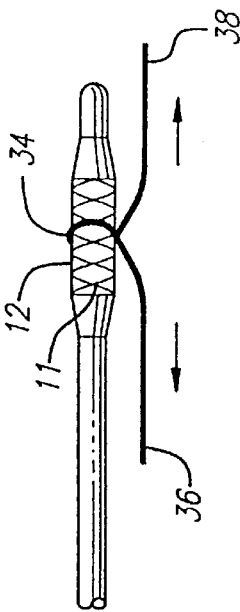
Figure 8:
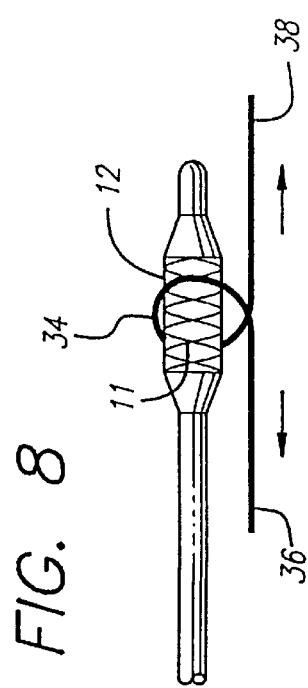
Figure 10:
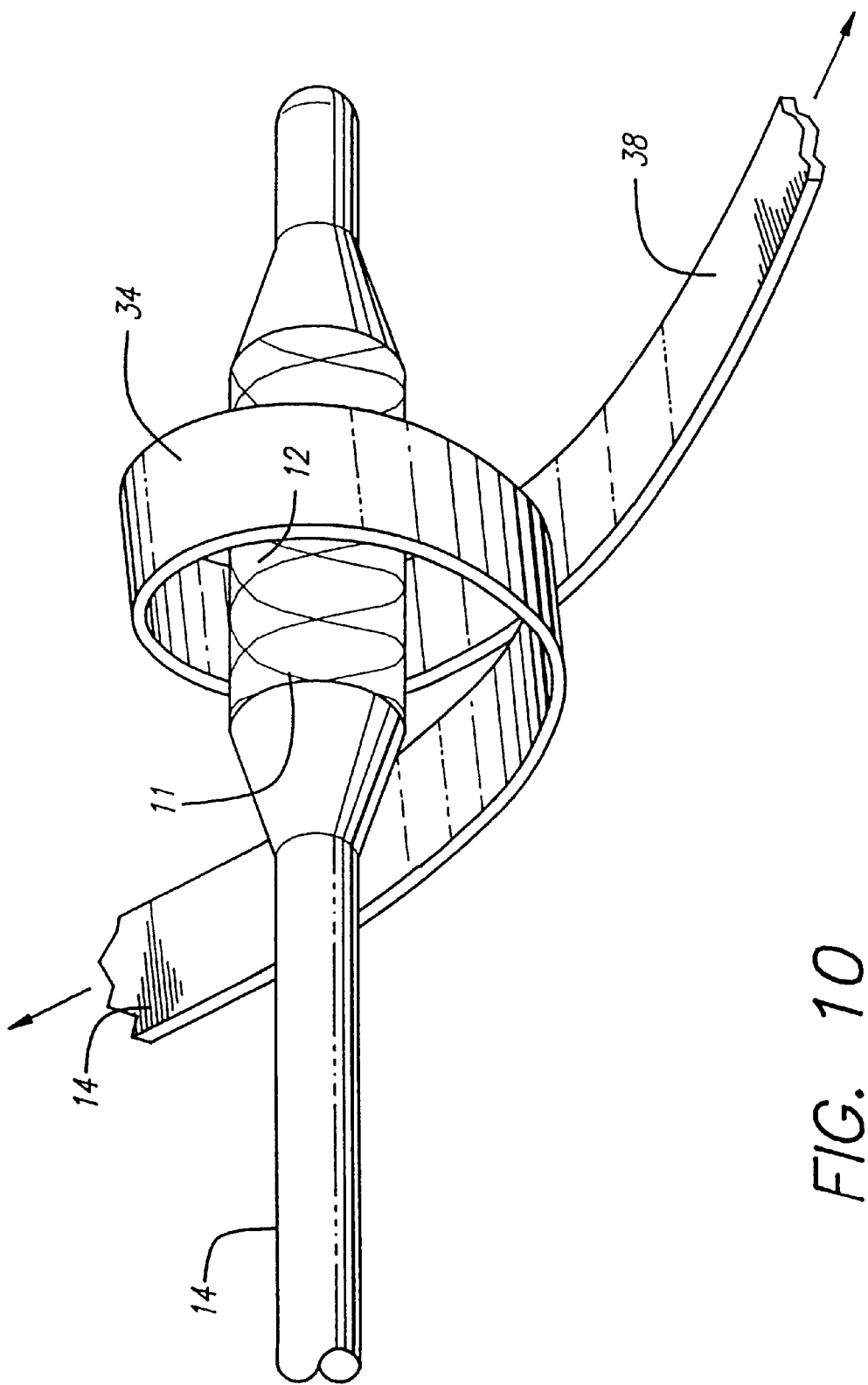
FIG. 10 is a perspective view of the cylindrical loop with the stent and the balloon portion of the catheter positioned within the loop.

The present invention provides for a crimping tool which uniformly and tightly crimps an expandable stent onto a catheter, such as a balloon catheter, so that the stent remains removably attached to the catheter until the stent and catheter are positioned in a body lumen. In keeping with the invention, device 10 comprises crimping tool 20 for enabling effective crimping of an intravascular stent 11 onto the collapsed balloon portion 12 adjacent the distal end 13 of a balloon catheter assembly 14. In the exemplary embodiment of device 10, as shown in FIGS. 1–5, crimping tool 20 is adapted to be held in the hand of the user, so as to enable stent 11 and catheter 14 to be supported in tool 20, and to enable the user to apply compressive force to tool 20 to crimp stent 11 on catheter 14.

Crimping tool 20 includes first handle member 22, second handle member 24 pivotally movable into engagement with first handle member 22 in a generally pendulum-like movement, and pin 26 pivotally connecting the upper portions of first handle member 22 and second handle member 24. First handle member 22 and second handle member 24 are engageable and generally complementary and preferably somewhat triangular in shape to ergonomically fit the hand, and include slots 28 and 30 therein which are preferably somewhat arcuate-shaped. Preferably, first handle member 22 is configured to receive second handle member 24.

Crimping tool 20 further includes crimping member 32 which is disposed within slots 28,30 which is adapted to receive stent 11 mounted on balloon portion 12 of the catheter assembly 14. Crimping member 32 includes cylindrical loop 34 having first end 36 and second end 38. First end 36 of cylindrical loop 34 is attached to first attachment member 40 on first handle member 22. Second end 38 of cylindrical loop 34 is attached by second attachment member 42 to second handle member 24. First attachment member 40 and second attachment member 42 can be of any design which can removably attach first end 36 and second end 38 respectively to the first and second handle members. As an example, first attachment member 40 and second attachment member 42 can include a snap or jaw-like member which grips first end 36 and second end 38 of cylindrical loop 34. It is intended, for example, that cylindrical loop 34 be replaceable when it wears out.

While cylindrical loop 34 can have various configurations to suit particular needs, a preferred embodiment is shown in FIG. 11. Thus, first end 36 of the cylindrical loop is attached to first attachment member 40 on first handle member 22 and second end 38 is attached by second attachment member 42 to second handle member 24. As indicated, the first and second attachment members can be of any design which can removably attach the first and second ends of the cylindrical loop to the handle members. In the FIG. 11 embodiment, apertures 44,46 are provided as convenient attachment means to correspond with a snap or jaw-like member on the handle members to help grip and removably attach first and second ends 36,38. A slot 48 is provided in the cylindrical loop to receive first end 36 to form the loop. Flanges 49 are provided to prevent the loop overtravel. The width 45 of the cylindrical loop should coincide with the length of the stent which typically is from about 6 mm to 30 mm. The width can be selected to accommodate either shorter or longer stents as necessary. Preferably, width 45 is selected so that the full length of the stent is covered by the cylindrical loop since it generally is undesirable to crimp less than the entire stent length at one time. The cylindrical loop can be formed of any non-stretchable material, and preferably is formed of Mylar or a similar flexible, but non-stretchable plastic material.

In a manufacturing context, the crimping tool can be used repeatedly to crimp stents onto the balloon portion of catheters. Repeated use will result in the cylindrical loop wearing out, whereby it should be replaced. Thus, it is contemplated that first attachment member 40 second attachment member 42 provide means for releasing the ends of the cylindrical loop and accepting ends of a replacement cylindrical loop for further use. Additionally, an adhesive may be used to permanently attach first end 36 and second end 38 to the handle members, for use in those situations where the crimping tool 20 is designed for a single-use application, as will be described.

Crimping tool 20 also is adapted for a single-use application, for example, by a cath lab physician or cath lab personnel. In that situation, crimping tool 20 can be discarded after the stent is crimped onto the balloon portion of the catheter. Further, first attachment member 40 and second attachment member 42 can be a permanent attachment, as opposed to a removable attachment to attach the ends of the cylindrical loop to the handle members.

In the preferred method of use, as shown in FIGS. 6–10, stent 11 is first positioned over balloon portion 12 by hand, and then catheter assembly 14 is moved within cylindrical loop 34 to receive the crimping procedure. For ease of illustration, FIGS. 6–10 depict loop 34 as having no or very little width, however, loop 34 should preferably have a width that approximates the length of the stent, which typically may be 20 mm or more as previously described for the FIG. 11 embodiment. First handle member 22 and second handle member 24 are compressed together thereby moving ends 36, 38 in opposite directions as depicted in FIGS. 6–9. As the opening of cylindrical loop 34 becomes smaller, the loop tightens around stent 11 thereby crimping it onto the balloon portion of the catheter. Reference indicia 50 on second handle member 24 corresponds to the size or diameter of cylindrical loop 34. Thus, one using the crimping tool can easily determine the crimping force, and importantly, the crimped diameter of the stent on the balloon portion of the catheter. Thus, the reference indicia correspond to the final diameter, or crimped diameter of the stent, thereby taking the guesswork out of the crimping procedure as it relates to the amount of force applied to the stent and the final crimped diameter.

The first and second handle members are biased open, such as by a coil spring or other biasing means, so that when the compressive force of the user's hand is released, the handles will move open and away from each other. When the handles move open, cylindrical loop 34 has enough resiliency in the material that it naturally will open, allowing the crimped stent and balloon catheter assembly to be withdrawn.

Figure 12B:
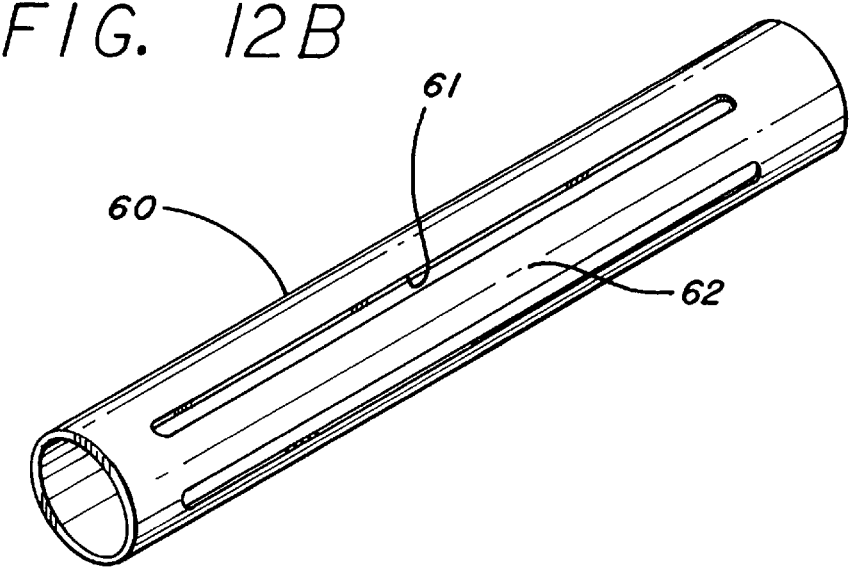
Figure 12C:
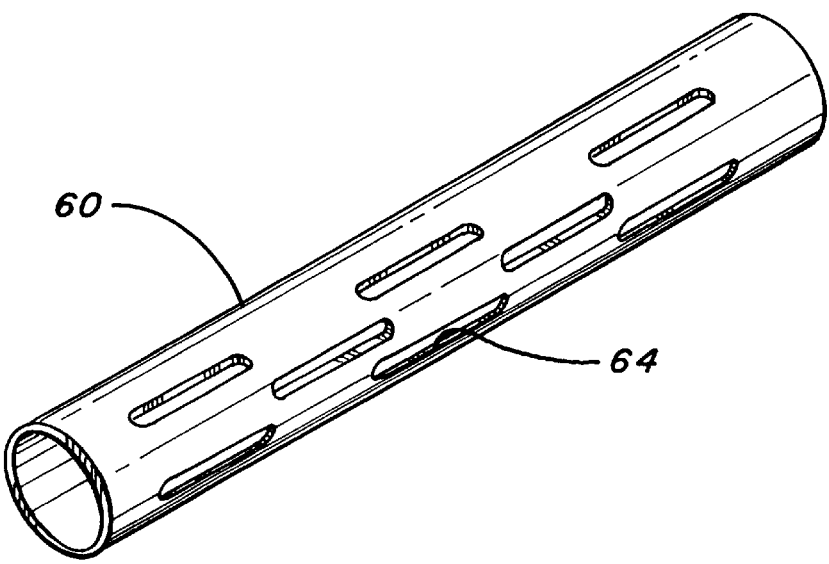

In each of the embodiments of the crimping tool, sheath 60 can be positioned over the stent, preferably prior to crimping the stent. The sheath can have various configurations such as those shown in FIGS. 12A–12C, and preferably has sufficient length and wall thickness to cover the stent and uniformly distribute the crimping forces applied to the stent by crimping tool 20. As the crimping tool applies force to the sheath, the force is evenly distributed over the sheath and hence to the stent. The sheath can be left on the stent after crimping and provide a cover to protect the stent in a safe manner until just before the stent is implanted in the patient.

In one preferred embodiment of sheath 60, slots 61 are formed in the sheath so that strips 62 in between the slots cover specific portions of the stent to prevent fish scaling during the crimping process. Fish scaling, which results from portions of the stent moving radially outwardly due to uneven crimping forces, can occur during the crimping process with some stent configurations. Thus, strips 62 are positioned over portions of the stent susceptible to fish scaling to counteract the effect and maintain a cylindrical geometry in the stent.

The sheath can be formed from an elastic material known in the art and can have various thicknesses depending on the particular stent configuration. Slots 51 or other apertures 54 are formed in the sheath using a laser or by other means known in the art. The sheath is removed prior to implanting the stent in the patient.

It is contemplated that the present invention crimping tool 20 can be used in a manufacturing facility having a sterile environment to be used multiple times to crimp multiple stents on catheter assemblies. It is also contemplated that the crimping tool 20 will be used for single use applications by cath lab personnel, where a stent is crimped onto the balloon portion of a catheter, and the tool is then discarded, since there is no assurance that the tool can be sterilized after the single use application in the cath lab.

While certain dimensions and materials of manufacture have been described herein, modifications can be made without departing from the scope and spirit of the invention.

While in the preferred embodiment the stent described is intended to be an intraluminal vascular prosthesis for use within a blood vessel, such as a saphenous vein, coronary artery, carotid artery, etc., and the balloon delivery catheter is of the same or similar to that used in therapeutic coronary angioplasty, it will be appreciated by those skilled in the art that modifications may be made to the present invention to allow the present invention to be used to crimp any type of stent onto any catheter. The present invention is not limited to stents that are deployed in a patient's vasculature, but has wide applications to loading any type of graft, prosthesis, liner or similar structure. Furthermore, the stent may be delivered and implemented not only into coronary arteries, but into any body lumen. Other modifications can be made to the present invention by those skilled in the art without departing from the scope thereof.

What is claimed is:

1. A device for crimping a stent onto a balloon catheter assembly, comprising:
   a pair of handles including a first handle member configured for pivotable engagement with a second handle member and a pivot pin extending through each of the handle members;
   a crimping member including a strip that is looped and having a first end and a second end, the first end being attached to the first handle member and the second end being attached to the second handle member;
   the looped strip forming a substantially cylindrical loop for receiving the stent and balloon catheter assembly, whereby the stent and balloon catheter assembly are positioned within the cylindrical loop and the first and second handle members are squeezed together so that the first and second ends of the crimping member move in opposite directions thereby constricting the cylindrical loop to a smaller diameter and forcibly compressing the stent onto the balloon catheter assembly.

2. A device as in claim 1, wherein the second handle member is configured to receive the first handle member when the handle members are squeezed together.

3. A device as in claim 1, wherein the first and second handles are ergonomically shaped in a substantially triangular-shaped configuration to fit the hand.

4. A device as in claim 1, wherein the crimping member is formed from a non-stretchable plastic material.

5. A device as in claim 4, wherein the non-stretchable plastic material includes material having a high tensile strength and a low elastic modulus.

6. A device as in claim 1, wherein the handles are formed from a rigid plastic.

7. A device as in claim 1, wherein the first handle member includes reference indicia relative to the second handle member so that the reference indicia correspond to the crimping diameter of the cylindrical loop.

8. A device as in claim 1, wherein the first handle member and the second handle member include a first attachment member and a second attachment member respectively associated therewith for attaching the first end and the second end of the crimping member to the first handle member and the second handle member.

9. A device for crimping a stent onto a balloon catheter assembly, comprising:
   first and second handles pivotably connected at a common location;
   a strip curved into a loop and having first and second ends, wherein the first end is attached to the first handle and the second end is attached to the second handle;
   wherein the stent and balloon assembly are positioned within the loop, and squeezing the handles pulls the first and second ends in opposite directions collapsing the loop and crimping the stent onto the balloon assembly.

10. The crimping device of claim 9, wherein the first and second handles each includes opposite ends and the handles are pivotably connected at a common end, and wherein each handle includes a slot formed adjacent to the hinged ends and the loop is disposed in the slot.

11. The crimping device of claim 9, wherein the strip includes a slot and the first end of the strip passes through the slot.

12. A method of crimping an intravascular stent onto a balloon catheter assembly, comprising:

positioning an intravascular stent over the balloon portion of the catheter assembly;

placing the stent and balloon portion of the catheter assembly in a radially compressible device;

disposing the stent and balloon portion of the catheter within a strip curved into a cylindrical loop having a pair of ends, the pair of ends being attached to a pair of handle members hinged for pivotal movement;

applying leveraged pivotably-engageable compressive force to the pair of handle members to pull the ends and collapse the loop to crimp the stent onto the balloon portion of the catheter; and releasing the compressive force, to enable removal of the crimped stent and the balloon portion of the catheter together from the radially compressible device.

* * * * *

UNITED STATES PATENT AND TRADEMARK OFFICE
CERTIFICATE OF CORRECTION

PATENT NO. : 6,051,002
DATED : Apr. 18, 2000
INVENTOR(S) : Stephen A. Morales

It is certified that error appears in the above-identified patent and that said Letters Patent is hereby corrected as shown below:

Title page, under "U.S. PATENT DOCUMENTS", add the following:
    --1,966,543    7/1934    O'Russa--.

Title page, under "FOREIGN PATENT DOCUMENTS" add the following:
    --0 938 880    9/1999    European Pat. Off.,
    297 14 857U   10/1997    Germany,
      0 303 889    2/1989    European Pat. Off.,
    975 797 A      3/1951    France--.

Title page, under "OTHER PUBLICATIONS", line 2, after "1977", delete "No Drawings are enclosed", and delete the duplication at lines 19 & 20, and line 24, after "1998", delete "Lost? Not available."

Signed and Sealed this

Third Day of April, 2001

Attest:

NICHOLAS P. GODICI

*Attesting Officer*    Acting Director of the United States Patent and Trademark Office